United States Patent [19]

Bailey et al.

[11] 3,961,521

[45] June 8, 1976

[54] TOOTH TESTING SYSTEM AND MACHINE

[76] Inventors: Ronald L. Bailey, No. 11 Flamingo, St. Peters, Mo. 63376; Joseph C. Muhler, R.R. 2, Sturgis, Mich. 49091; Mark S. Putt, 4034 Westlane Drive, Fort Wayne, Ind. 46805

[22] Filed: May 31, 1974

[21] Appl. No.: 474,960

[52] U.S. Cl. ................................................. 73/7
[51] Int. Cl.² ............................................ G01N 3/56
[58] Field of Search ........................................ 73/7

[56] References Cited
UNITED STATES PATENTS

| | | | |
|---|---|---|---|
| 2,189,589 | 2/1940 | Mahannah et al. | 73/7 |
| 2,323,175 | 6/1943 | Young et al. | 63/7 |
| 2,660,055 | 11/1953 | Thommen | 73/7 X |
| 3,216,238 | 11/1965 | Bailey | 73/7 |
| 3,555,877 | 1/1971 | Thelin | 73/7 |

OTHER PUBLICATIONS

"Test for Resistance of Porcelain Enamels to Surface Abrasion", Porcelain Enamel Institute, Inc., Product Standards Section, Mar. 1942, pp. 4–11.

*Primary Examiner*—Charles A. Ruehl
*Attorney, Agent, or Firm*—Rogers, Eilers & Howell

[57] ABSTRACT

A system and machine, or orbital brushing simulator, especially designed for testing the effect of cleaning and polishing agents and of brushes on tooth or similar specimens, with particular respect to enamel, dentin, or cementum abrasion, enamel or dentin polishing, enamel scratching, and cleaning. The machine accommodates several individually-mounted specimens, each acted upon by a brush moving over it in either of two directions, or in combinations of the two, thereby avoiding grooving of the specimen surfaces as well as providing more flexible and useful patterns for study. The system has a gravity-operated mechanism to set the pressure between each specimen and its brush, which thereby avoids variation in the pressure in a test involving a substantial number of cycles. This means is adjustable to provide very light pressures that are nevertheless steady. Means are provided to maintain a uniform suspension of the cleaning and polishing agent during the testing operation. The speeds and ranges of the brush movements in the two directions are separately adjustable; counters are provided for setting and indicating the number of brushing cycles to be performed; and the machine stops upon cycling the respective number, then reverses itself at an appropriate speed to the extent necessary to return the machine to neutral or its centered position in each axis, after which it ceases operation.

29 Claims, 11 Drawing Figures

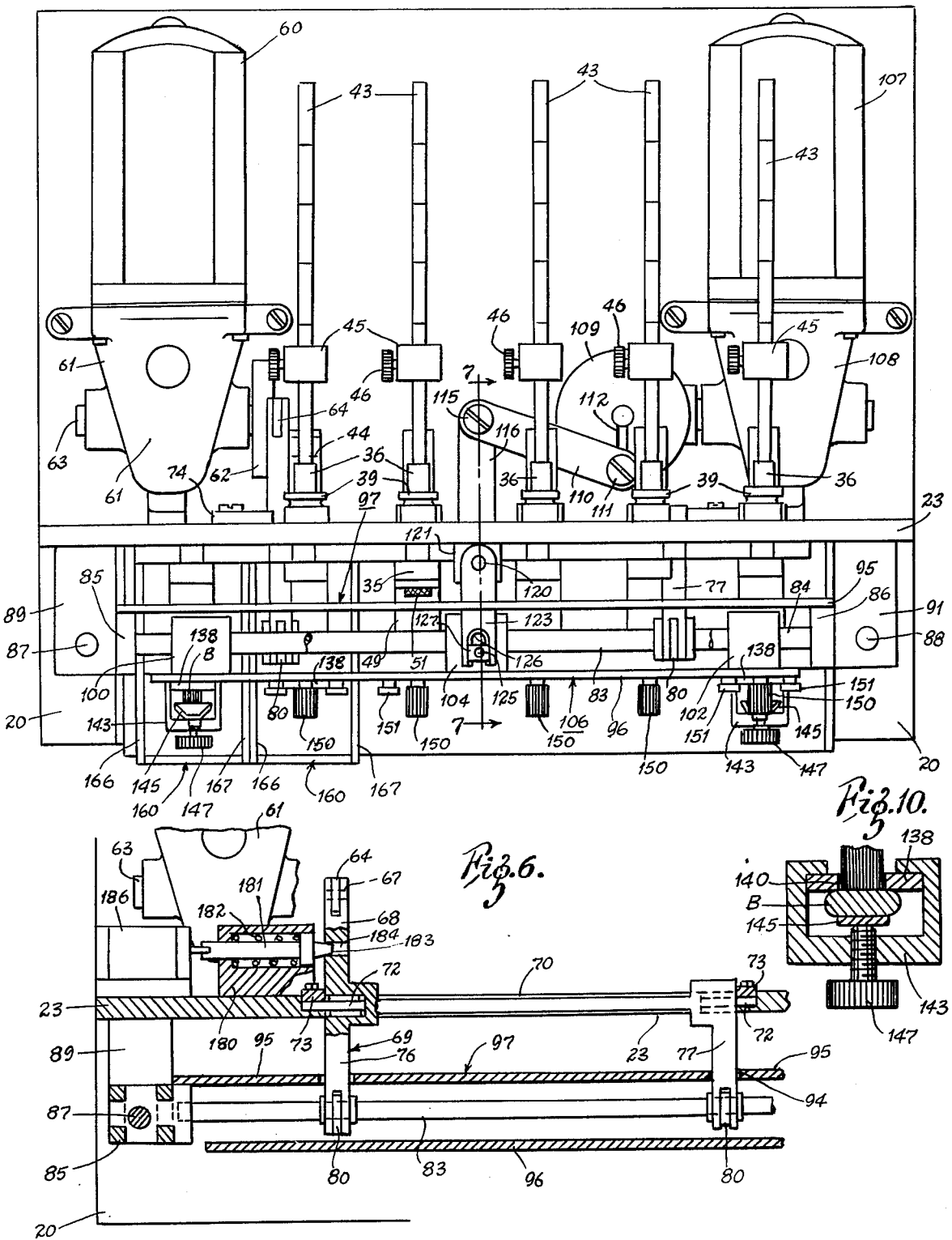

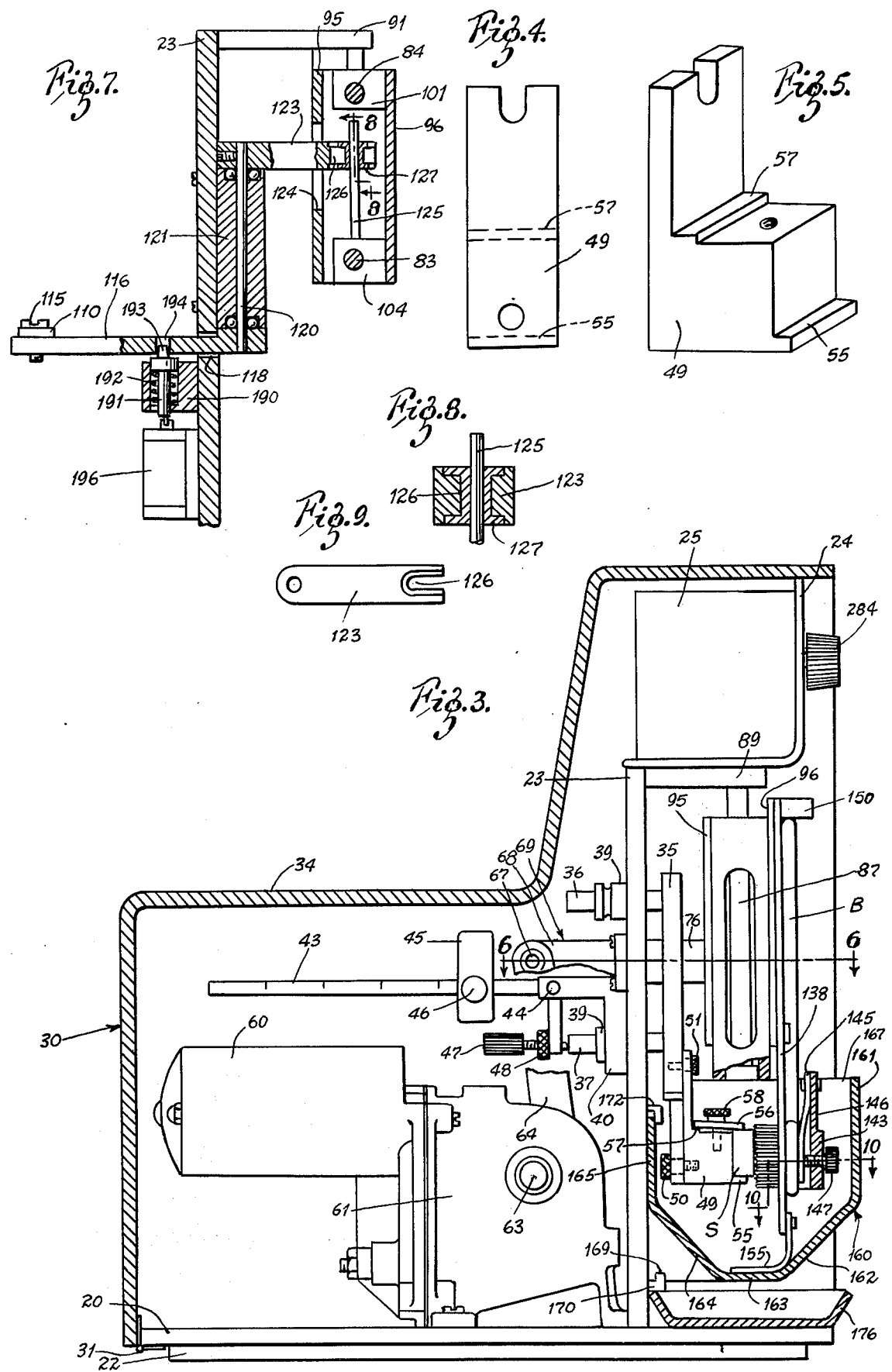

TOOTH TESTING SYSTEM AND MACHINE

BACKGROUND AND FEATURES OF THIS INVENTION:

The principal machine heretofore used for the purposes of testing tooth or similar specimens is the so-called cross-brushing machine, designed over 25 years ago and using only linear relative motion of the brush and tooth specimen, in a single direction. As a result, the repeated cycling, for example, into thousands of cycles, results in linear grooving of the dentin or enamel, making it very difficult, and in most instances impossible, to obtain significant and uniform data, and making the system very sensitive to the orientations of the specimens in the apparatus recording the test results.

The cross-brushing machine also has the disadvantages of using spring-operated means in order to maintain pressure between the specimen and its brush. When that machine performs a large number of cycles, the spring fatigues, giving erratic pressures leading to erratic and unreliable laboratory results, depending upon the number of times the spring is cycled and used. A further problem lies in the fact that in recent months one could not obtain consistent springs for replacement. The present instrument overcomes these problems by using a scale beam type of force means to apply pressure between the specimen and its brush, which means result in maintaining the same pressure throughout the test regardless of the number of cycles, and which is not subject to the fatigue problem. The force may, as noted, be very light, if desired for certain tests such as polishing studies, or very strong, as required for abrasion evaluation. Furthermore, the means is readily and accurately adjustable.

The cross-brushing machine also has the problem that the moving members of each brush specimen pair do not move in a vertical direction, and as a result did not prevent stratification and settling in the liquid carrier of finely-divided particles of the medium being tested. This also results in unreliable and irregular results. The present instrument employs a vertically movable brush holder with an agitator that is immersed in the liquid carrier, and constantly maintains pace with the movement of the movable member in order to agitate and maintain the liquid suspension homogeneous throughout the test.

Another feature of the present invention is that each brush and specimen are maintained in an unvarying planar relationship during the movements of the brush across the specimen. This result is obtained by having the specimen move toward and away from the brush in a rigidly-maintained fore-and-aft path, at right angles to the movements of the brush. The brush holder is held firmly for movements in its plane of operation and the brush is held against any rocking or twisting movements in the holder.

The present instrument has six stations for specimens, each comprising a specimen and a brush in a slurry cup, with the scale beam means to urge the brush and the specimen together. The scale beam means, in addition to the advantages above recited, facilitate calibration of the brush pressures which may be set individually for each station by a simple sliding adjustment of poises along the beams. The transmission apparatus for delivering the force of the scale beam to the brush-specimen interfaces is highly friction-free and the movements are horizontal in order to eliminate a need for counterbalance. The machine provides brush pressure of 100–500 grams linearly and parallel to the specimens.

There is a separable specimen clamp and a removable brush carrier for each station, so that brushes and specimens may be selected as desired for each station. As noted, the brush clamps are designed in order to insure parallelism of the brushes with their specimens during their relative movements. Each specimen is mounted on a carrier with a viseclamp that is secure, but which can be easily removed and replaced for mounting of the specimens in the vise outside the machine. The vise clamp engages the head of the brush, which is the part thereof that is flat and which can be used to assure the proper alignment of the brush and specimen.

This machine has individual slurry cups, one for each specimen. The brush holders and brushes move in a vertical plane, dip into the slurry cups, and have flexible agitators attached to the lower ends of the brush holders. The cups have sloping bottom walls that cooperate with the wiping agitators in order to insure full pickup of the material being tested and reduce or eliminate settling of the small particles which occur inherently in a polishing system. The slurry cups are of a shape to fully immerse the specimens, their holders and mechanisms in the liquid containing the material being tested. Also, there is a full length removable drip tray below the cups.

The entire mechanism is accessible, particularly the parts subject to wear. Interengaging moving parts are maintained spaced from the slurry, and particularly are above it so as to minimize gravity effect in delivering abrasive slurry to them.

This machine produces movement between the brushes and specimens in either an X or a Y direction (i.e., vertical or horizontal), or a combination of both, which avoids deep scratching caused by repeated brushing back and forth along the same parallel line. This renders the specimen, after test, insensitive to its orientation in the recording device which is used to evaluate the effects of the experimental design. The older cross-brushing machine produced rectilinear grooves all in the same direction and as a consequence, the response of the recorder which measures polishing or cleaning depends upon whether the specimen is read crosswise or lengthwise of the grooves — i.e., the reading depends upon orientation of the specimen in the recorder. As a result, one may obtain almost any data he wishes depending upon the orientation and placement of the specimen.

The range of movement, and the speed, of the brushes are individually adjustable for each of their two directions of movement. The stroke adjustment in the vertical direction is 0–2.54 centimeters, and that in the horizontal is one-half that amount.

Count-down pre-set counting means are provided. These can be set to be controlled by the cycles of either axis. When the machine reaches the respective count, it automatically reverses the motors of both axes until the machine is centered at its starting positions for both axes, after which it stops. It then can be restarted by resetting the counter, assuming the appropriate manual switches are closed.

The control may thus be effected by counting either the X-axis or the Y-axis cycles, as desired by the operator, or the present counter may be manually bypassed and the machine operated by manual control.

A calibration circuit is provided in order to enable the speed to be calibrated with respect to the dials.

Other features than those described above will appear from the full description which is to follow.

In the drawings:

FIG. 2 is a top view of the instrument with the cover removed;

FIG. 3 is an end elevation partly in section taken substantially approximately immediately inside the cover at the left end of FIG. 1, some parts being broken away;

FIG. 4 is a back view, somewhat enlarged, of one of the specimen vises shown in FIGS. 1–3;

FIG. 5 is an isometric view of the vise shown in FIG. 4;

FIG. 6 is a view in horizontal section taken approximately on the line 6—6 of FIG. 3;

FIG. 7 is a vertical section taken approximately on the line 7—7 of FIG. 2;

FIG. 8 is an enlarged fragmentary view taken approximately on the line 8—8 of FIG. 7;

FIG. 9 is a plan view of the over-arm of FIG. 7;

FIG. 10 is an enlarged section through a brush holder taken on the line 10—10 of FIG. 3.

DESCRIPTION OF THE PREFERRED EMBODIMENT

Figure 1:
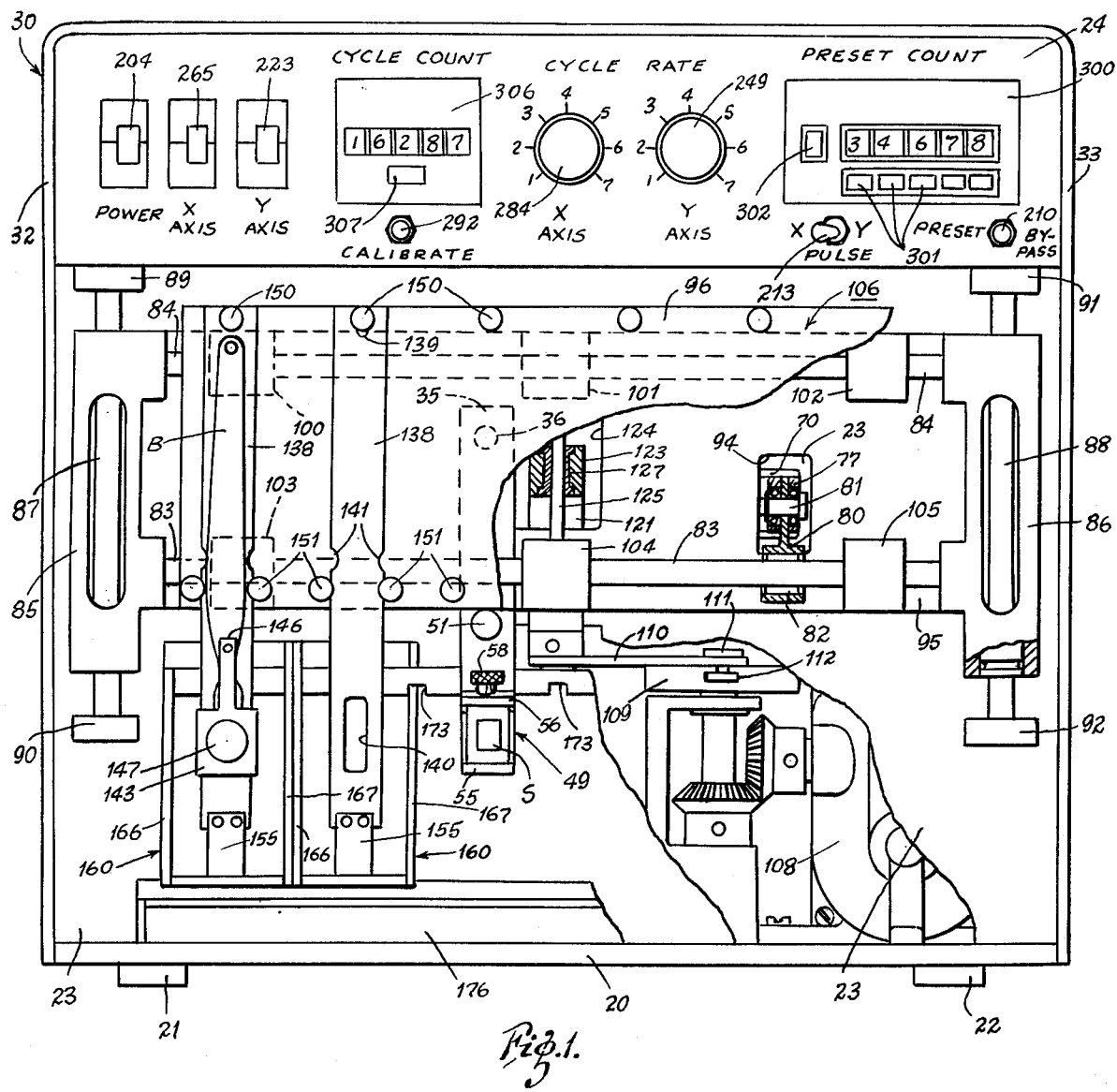
FIG. 1 is a front elevation with parts removed, or progressively broken away beginning at its left side, in order to show the instrument at different depths toward the rear.

The machine has a base plate 20 that may rest on two elongated feet 21 and 22. A vertical partition 23 extends upwardly, is secured firmly to the base 20, and constitutes the principal vertical support for many parts of the instrument. An angular control and instrument panel 24 has one side secured to the top of the vertical plate 23 to support a group of instruments and control components that are here diagrammatically and collectively represented by the box 25. All of the parts 20 through 24 are preferably made of metal and are rigidly secured together by welding, bolting, or the like.

There is also a cover 30 that is hinged at 31 to the base. The cover has side panels 32 and 33, and a compound top 34 that extends upwardly from the rear of the base 20, then forwardly horizontally, then sloping upwardly and forwardly, and finally forwardly horizontally to overlie the upper edge of the instrument panel 24, to which it may be latched.

The machine is adapted to hold a plurality, here six, tooth specimens, and an equal number of brushes. The specimens are individually mounted on the panel 23 in a manner that causes each of them to be urged forwardly with adjustable, predetermined force against the brushes mounted in front of them. The predetermined force establishes a brushing pressure. The brushes are mounted on the panel 23 and are provided with a compound of movements in two directions, with the speed and extent of movement in each direction individually adjustable from zero to a predeterined maximum.

The specimen carriers will be described first. All of the specimens are mounted in the same manner, so that only one of the carriers need be described.

An elongated, vertical specimen carrier or support 35 has two circular shafts 36 and 37 fixed firmly to it and extending backwardly from it. These shafts 36 and 37 pass through ball bushings 39 mounted in the panel 23. The two ball bushings and the two shafts provide very accurately controlled forward and backward movement of the carrier member 35 on the panel 23 with a minimum of friction.

An L-shaped bracket 40 is fixed to the back side of the pane 23, and may surround the outside of the lower bush bearing 39. The outer end of its horizontal arm is bifurcated to receive a bellcrank scale beam 43 pivoted to the bracket 40 at 44 for free pivotal movement. The horizontal arm of the bellcrank 43 is calibrated, and slidably receives a counterpoise 45 that may be adjusted along the arm to apply a predeterminable force to the vertical arm of the bell crank which depends adjacent the backwardly projecting end of the shaft 37. A screw 46 can secure the weight in adjusted positions.

The vertical arm of the beam 43 has an adjusting screw 47 threaded through it, having a lock nut 48. The screw 47 abuts against the end of the shaft 37. As will be evident, by adjusting the screw 47 in or out and then setting its position with the lock nut 48, the arm 43 can be made horizontal so that the force vector of the weight can act fully against the shaft 37 and the specimen, urging the specimen-supporting member 35 forwardly. As the movements of the specimen carrier in the bearings 39 is horizontal, no gravity counterbalance is required.

A specimen vise 49 is mounted on the lower end of each specimen support arm 35. This vice receives a shouldered screw 50 threaded into its lower end at the back and shouldered screw 51 at its upper end. The shouldered screw 51 is adapted to be slipped snugly into a notch that bifurcates the upper end of the vise 49, after which the shouldered screw 50, passing through an opening in the support 35, is threaded into the vise element 49. The shouldered screw 51 may be tightened to securely hold the vise 49 on the specimen-support member 35.

The vise member 49 has a bottom ledge 55 at its forward end, on which a specimen block S may rest. The upper end of the specimen is clamped by a clamp plate 56 that spans from the top of the specimen back to a ledge 57 on the vise 49. The plate 56 is forced down by a screw 58 to clamp the specimen between the plate and the ledge 55. It will be seen that the medial portion of the clamp plate 56 is held above the upper principal surface of the vise 49 by the fact that the shoulder 57 and the specimen S project above that surface. This permits the clamping action to be effected.

As illustrated, there are six specimen holders, like the one described, each of which is urged forwardly by a force individually determined by the position of its weight 45 along its beam 43. The specimens are urged by these forces into contact with toothbrushes, the mounting of which is now to be described. The means to provide vertical movements of the brushes will be described first, followed by description of the horizontal movement means. It will be recognized that other devices than toothbrushes may be used, as the rubbing means, although toothbrushes have a particular value in testing dentifrices, mouthwashes containing polishing agents, and the like.

For vertical movements of the brushes, there is a motor 60 with a gear-reducing transmission 61 mounted on the base 20. This motor rotates a drive wheel 62 mounted on the motor shaft 63. A connecting link 64 is pivotally connected eccentrically to the wheel 62 in one of several positions of different eccentricity in a manner known in the mechanical arts. The upper end of the like 64 is rockably attached at 67 to the bifurcated end of an arm 68 of a horizontally disposed H-shaped driver generally indicated at 69 (FIG. 6). A slot 70 is provided through the panel 23 to receive the driver 69, which is rockably mounted at the ends of the slot 70 on pivots 72 that have antifriction bearings. The panel 23 has notches cut in from its back face, in order to accommodate the pivots 72. These notches are closed by blocks 73, which in turn are held in place by screws. This arrangement provides for rocking movement of the driver 69 when the electric motor 60 operates in order to drive the connecting link 64.

The driver 69 also has forwardly extending arms 76 and 77 on the front side of the panel 23. The two arms 76 and 77 are bifurcated at their forward ends and embrace connecting rods 80, to which they are pivoted at 81 with appropriate anti-friction means (FIG. 1). The connecting rods 80 at their lower ends have anti-friction bearing mountings 82 onto a horizontal X-axis rail 83, here in the form of a cylindrical rod. Another like rail 84 is parallel to the rod 83 and above it. The opposite ends of these rods 83 and 84 are mounted in platform carriers 85 and 86 at opposite sides of the machine, the carriers being supported for vertical movement on vertical rods 87 and 88 with ball bushings to minimize friction.

The vertical rod 87 is supported between top and bottom members 89 and 90, while the vertical rod 88 is mounted in corresponding members 91 and 92. These members 89, 90, 91 and 92 are firmly secured to, and extend forward rigidly from, the vertical partition or panel 23. They also aid in supporting the instrument panel 24. A panel 95 is attached rigidly to the back of the two platform carriers 85 and 86 by appropriate means, as shown in FIG. 2. This assembly of rods 83 and 84, carriers 85 and 86, and the panel 95, is generally designated as the "X-axis plaatform 97". It provides a rigid support platform having true vertical movement on the rods, with minimal friction. The panel 95 has holes 94 to admit the arms 76 and 77 of the driver 69, and a hole to admit the Y-axis drive as will appear later.

From the description so far, it can be seen that rotation of the motor 60 drives its eccentric 62 which rocks the link 64, and that link in turn rocks the generally-horizontal disposed X-axis driver 69 about its pivots 72 in the partition 23. The movement results in up-and-down arcuate movement of the arms 76 and 77 of the driver 69, which by virtue of their connection to crank arms 80 that in turn are connected to the shaft 83, produces ultimately a vertical reciprocation of the X-axis platform 97.

There is also a front panel or plate 96 movably mounted on the platform 97. It is secured firmly to and supported on bearing blocks 100, 101, 102 that slide on the upper shaft 84, and corresponding ones 103, 104 and 105 that slide on the lower shaft 83. Each of these bearing blocks has in it a ball bushing, to provide free and accurate reciprocation along the shafts. The panel 96 and the blocks 100-105 constitute the Y-axis platform 106.

The means for producing horizontal reciprocation of the Y-axis platform 106 includes an electric motor 107 supported on the base 20 and operating through a transmission and reducing gear 108 and appropriate shafting to turn a horizontally-disposed eccentric wheel 109. A crank arm 110 is pivoted at 111 to the wheel 109 and also is pivoted at 115 to a crank arm 116.

As illustrated in FIG. 2, the pivot 111 is arranged to provide an adjustment of the end of the link 110 toward or from the center of the wheel 109, by which the amount of lateral movement of the Y-axis platform may be adjusted. This is illustrated as a T-slot 112 in the wheel 109, in which a headed screw fits, the details of which need not be described because they are conventional. Another and sometimes preferred arrangement is to provide separate threaded holes for the screw 111 at different distances from its center, in the wheel 109. Suffice it to say that the arrangement permits the pivot axis to be moved into positions that are at different distances from the axis of the wheel 109.

The link 116 extends through a hole 118 in the partition 23 (esp. FIG. 7) and at its outer end has an anti-friction bearing that receives the lower end of a vertical spindle 120 supported in a sleeve 121 secured to the front surface of the partition 23. The link 116 is secured to the shaft to oscillate it. At its upper end the spindle 120 is securely and non-rotatably mounted in a Y-axis overarm 123 that extends forwardly through an opening 124 in the plate 95 to overlie the bearing block 104 that is one of the three bearing blocks of the Y-axis platform 106. Another vertical spindle 125 is mounted in the bearing block 104, extending upwardly therefrom and passing between the front bifurcations of the arm 123 that provide the slot 126. This bifurcated end of the arm 123 is rabbeted top and bottom so as to retain a spool-shaped sintered bearing 127 that may move lengthwise in the slot 126 of the arms, and that slidably and rotatably engages over the spindle 125.

By the foregoing arrangement the rotation of the wheel 109 by the motor 107 rocks the link 110, that rocks the line 116, which latter oscillates the spindle 120 in the bearing block 121 and causes the overarm 123 to oscillate. The elongated slot 126 of the bifurcated end of the overarm 123, engaging the spool-type bearing 127, causes the spindle 125 to be moved to the right or to the left, carrying with it the Y-platform 106 of which it is a part. All of these parts are sufficiently rigid that the movement is solid throughout the Y-axis platform assembly 106, and it results in the reciprocation of that platform. As previously noted, this platform is moved vertically by the operation of the motor 60, since it is mounted on the X-axis platform 67. The two movements may occur at the same time, producing a compound movement of the platform 106.

The platform 106 is designed to support the brushes that are to operate upon the specimens. Each brush is mounted upon a separate brush holder, and the brush holders are individually mounted upon the panel 96. Six brush holders are shown. They are identical so that only one of them will be described.

Each brush holder comprises an elongated strip-like rigid carrier 138 having a notch 139 extending inwardly from its upper end, and a bristle-transmitting hole 140 at its opposite end. It has two opposed notches 141 in its sides about midway between top and bottom. There is a brush clamp 143 that slides onto the bottom of the elongated brush carrier 138 adjacent the bristle hole 140.

As can be seen from the drawings, a toothbrush B with the characteristic handle and bristles is laid along the brush carrier 138 with the bristles extending through the hole 140. The brush clamp 143 is then slipped over the end of the brush carrier 138. As appears from the drawing (esp. FIG. 10), the brush clamp 143 has a channel shape, with inturned flanges that engage the back edges of the brush support 138 when the carrier is fitted over that support. A flexible pressure strip 145 is attached to the upper end 146 of the brush clamp. A pressure screw 147 extends through the bight portion of the brush clamp 143 and presses against the pressure strip 145 to urge the same against the rigid part of the brush B and to clamp the brush firmly against the brush carrier. By having the clamp force the head of the brush against the carrier 138, the greatest degree of stability and the best alignment of the brush for contact with the specimen is assured. The brush is positioned regardless of any bend in the handle, and the curved cross section of the brush handle cannot interfere with accurate and squared positioning, as the brush head has a surface adjacent the bristles that occupies a plane at right angles to the bristles.

The panel 96 has brush carrier top thumb screws 150 at its upper edge, with one for each of the brush carriers 138. Also, it has an opposite pair of fixed side clamp knobs 151 adjacent the bottom of the panel 96 in order to engage the opposite edges of each brush carrier. These knobs are flanged with the flanges spaced from the surface of the panel 96 by a distance appropriate to the thickness of the brush carrier 138.

With this arrangement, each brush carrier is first located in a position with the upper end of the carrier 138 below the top screw 150, and the opposite notches 141 slipped over the enlarged heads of the two brush clamp knobs 151. The brush carrier 138 is moved upwardly so that notch 139 enngages under the top brush clamp knob 150, and the notches 141 are moved upwardly from the two brush clamp knobs 151. The knob 150 is screwed down tightly, securing the brush carrier and brush to the Y-axis platform. The brush bristles are disposed directly opposite the specimen S, which is urged against the bristles by a force determined by the position of the weight 45. Each brush carrier 138 has a strip of flexible plastic 155 secured to its lower end as an agitator, for a purpose to later appear.

Cups, to hold liquid suspensions, are provided for the specimen positions. These may be clear plastic, and being identical, only one will be described.

The cup, designated generally at 160, is shown as being formed of a bent sheet of material that provides an upper front wall 161, a backwardly and downwardly sloping wall 162 below the front wall, a horizontal bottom wall 163, an upwardly and backwardly sloping wall 164 and a vertical back wall 165. There are two opposite side walls 166 and 167. The side walls at the bottom extend from the bottom wall 163 back to the back of the cup, and are notched at 169.

A bottom rail 170 is secured near the bottom of the front surface of the partition 23, and provides an upstanding edge that can be engaged by the notches 169 of the cups. An upper cup-receiving rail 172 secured to the partition 23 has a depending lower edge spaced outwardly from the partition 23 and provided with spaced notches 173. The back edge of each cup can be hooked under the depending flange of the rail 172 with the opposite side edges of the cup engaging in a pair of the notches 173. As shown in FIG. 3, the cup may be lifted under the rail 172 far enough to permit the notches 169 in the two lower side walls of the cup to be hooked over the upstanding flange of the bottom rail 170. When this is completed, the cup will surround the lower specimen support members and the lower part of the brush devices. The plastic strip 155 extends downwardly into the cup and tends to scrape the bottom thereof. It is adapted to act as a stirrer.

Below the cups 160 is a pan 176 that will catch any spill from the cups.

There is a lock means selectively operatable to lock either one of the two X or Y movement-producing mechanisms in a medial position. FIG. 6 shows this arrangement for the X-axis: and FIG. 7 shows the mechanism for the Y-axis.

As shown in FIG. 6, the X-axis driver 69 is pivoted at 72 in the partition 23 so that vertical rocking movement of the link 64 will cause the driver to produce vertical reciprocation of the shaft 83. Mounted on the back of the partition 23 is a lock pin housing 180 in which a lock pin 181 slides, it being moved to the right in that figure by a coil spring 182 acting between the housing and an enlarged shoulder on the pin 181. The end of the pin has a tapered tip 183 that is urged by the spring 182 into a hole 184 through the driver 69. The hole 184 is so located that when the self-centering pin 183 engages in the hole, the arm 69, as well as the structure attached to it, is firmly held in a middle position.

The pin 181 extends outwardly to the left of the housing 180 in FIG. 6 and is attached to the core of a solenoid 186 that is mounted onto the back of the partition 23. When the solenoid is energized, the pin is withdrawn from the hole 184 and the arm 69 is permitted to reciprocate fully. In order to prevent damage to the parts by a sudden stop of the motor, in the event the solenoid is de-energized while the motor is operating at full speed, a resilient drive connection is provided for the wheel 62. This may be a friction clutch or other such conventional means.

FIG. 7 shows a similar arrangement for the Y-axis control. In this case the locking mechanism engages the link 116 that is rocked by the motor 107.

There is a lock pin housing 190 mounted on the back side of the partition 23, just below the link 116. A lock pin 191 reciprocates in this housing and is urged upwardly by a spring 192 acting between the housing and a shoulder on the pin. The tapered point 193 engages in the hole 194 through the link 116 so that there is a self-centering action. When the pin is thus engaged the link 116 is firmly held in a medial position.

A solenoid 196 supported on the partition 23 is connected to the pin 191 and when energized withdraws the pin from the link 116.

Figure 11:
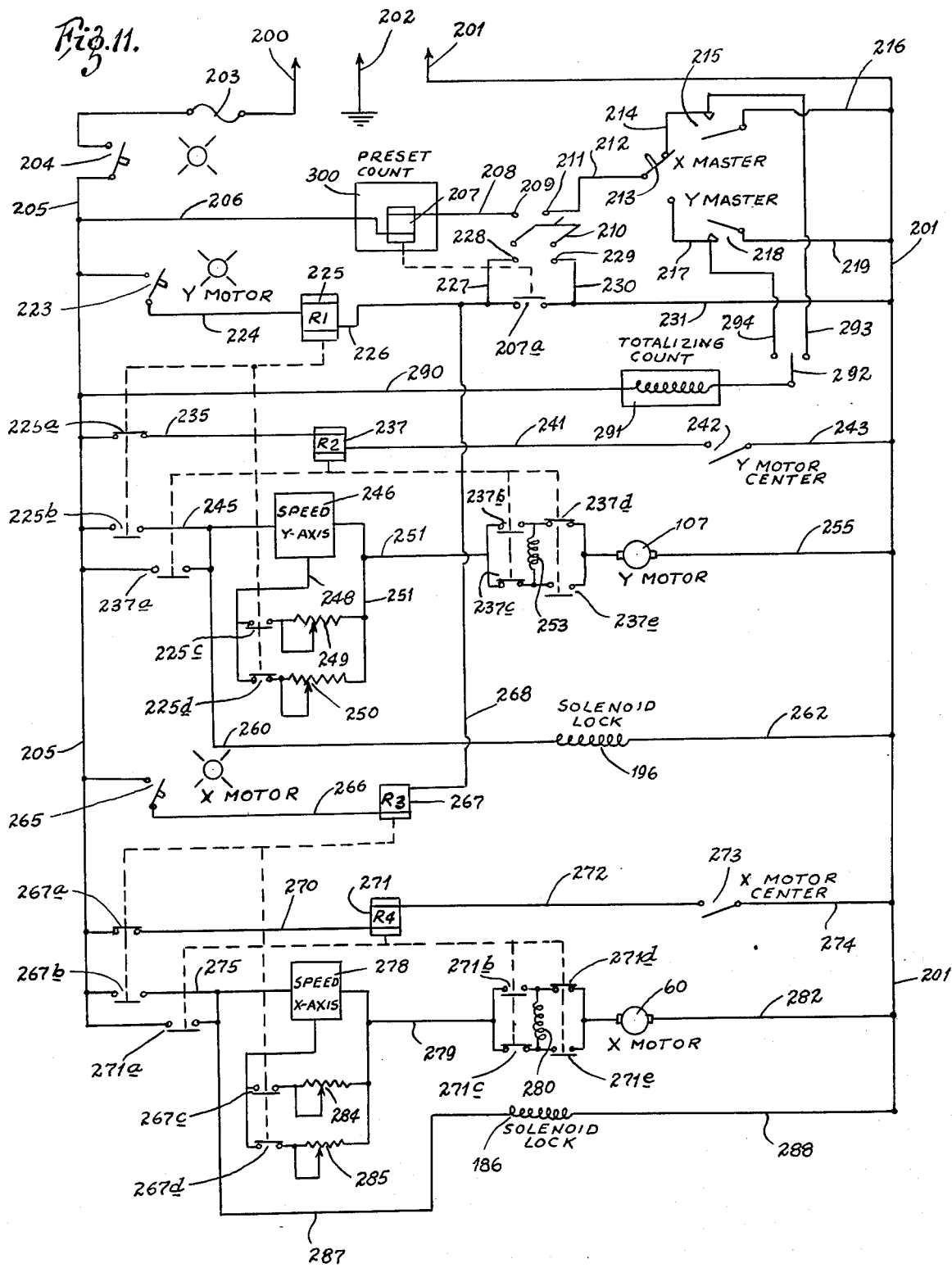
FIG. 11 is a wiring diagram of the machine.

The wiring diagram, FIG. 11, shows three power lines 200, 201 and 202, the last being a ground wire. Power line 200 goes through a fuse 203 to a manual main power switch 204 that appears on the control panel and is adapted to connect and disconnect a wire 205 to the wire 200.

At the upper part of the wiring diagram there is a wire 206 connected to the wire 205 that is subject to the main control switch 204. The wire 206 leads to a relay coil 207, that is part of a pre-set counter mechanism later to be described. The coil 207, when energized, opens a normally closed switch 207a in a circuit to be described. From the coil 207, a wire 208 leads to a contact 209 of a double-pole double-throw manual switch 210. The other terminal 211 of this double-throw switch is connected by a wire 212 to a manual switch 213 that can be manually set either to its upper X position or its lower Y position. It is illustrated in its X position wherein it connects the wire 212 to a wire 214 connected to a switch 215. This switch 215 is closed momentarily with each count of the X-axis motor to be described. Normally this provides a pulse delivered with each revolution of the X-motor. When the switch 215 closes, it connects the wire 214 to a wire 216 that is connected to the power line 201.

The Y side of this network, from the manual switch 213, includes a wire 217 connected to the manual switch 213 and thence to the Y pulse switch 218 that closes momentarily each revolution of the Y motor. The other side of this switch 218 is connected by a wire 219 to the power line 201. Thus the user may manually move the switch 213 to select whether he wishes to effect control by pulses of the X or the Y motor.

Returning to the power wire 205, there is a Y motor manual switch 223 for connecting the wire 205 to a wire 224. The wire 224 leads to relay coil 225, also designated R1. This relay coil 225, when energized, controls four switches that are shown connected to it by dashed lines. They include the switch 225a normally closed, a normally-open switch 225b, a normally-open switch 225c, and a normally-closed switch 225d. The functions of these switches will be described later. The other side of the coil 225 is connected by a wire 226 to a parallel switch network. This includes a wire 227 leading to a contact 228 of the double-throw double-pole manual switch 210 that can be closed with a contact 229. The contact 229 is in turn connected by a wire 230 to the wire 231 that is connected to the other power line 201.

Also, the switch 207a can connect or disconnect the wires 226 and 231. If after closure of the manual switch 223, either the switch 207a is closed, or the switch 210 is closed with the contacts 228–229, the relay coil R1 will be energized, shifting its switches 225a–d.

At the start, a centering circuit for the Y-axis motor may be energized. This circuit extends from the wire 205 through the normally-closed relay switch 225a, to a wire 235, by that wire to a relay coil 237 that shifts normally-open switches 237a, 237b, 237e and normally-closed switches 237c and 237d. From the coil 237, a wire 241 leads to a Y-motor centering switch 242 that is closed when the Y-motor is out of its proper starting position wherein the mechanism is centered. From the switch 241 a wire 243 leads to the other power line 201. This circuit is energized only when the relay 225 is de-energized and the switch 225a is closed.

When the coil 225 is energized, the switch 225b is closed. The switch 225b is connected by a wire 245 to a speed rate control 246. This control includes a diac type arrangement such that the energy transmitted can be controlled by variable resistances. Two such resistance sets are shown. A wire 248 leads from the control 246 to the relay switches 225c and 225d. The relay switch 225c is connected into a variable resistance 249 (see adjustable knob 249, FIG. 1), and the relay switch 225d is connected into a variable resistance 250. The parallel resistances are connected to the output of the control by a wire 251. The parallel resistance circuits are alternately energized by operation of the coil 225.

The output wire 251 connects into a reversing network for the Y-axis motor. The forward circuit through the reversing network runs from the wire 251 through the normally-closed switch 237c, thence upwardly through the field winding 253 of the motor 107, through the normally-closed switch 237d, through the Y motor 107 and by wire 255 to the other power line 201. Should the coil 237 be energized, the switches 237b through 237e will all be shifted, and the circuit from the wire 251 passes through the switch 237b downwardly through field winding 253 of the motor 107, through the switch 237e, the motor 107 and the wire 255 of the other power line 201. The motor 107 is series wound, and arranged so that the reversal of the direction of the applied field current reverses the direction of rotation of the motor. The speed of the motor is regulated by varying the applied voltage through the resistance networks of the diac.

The solenoid lock for the Y motor is also energized off the wire 245 that is subject to the switches 225b and 237a. The lock circuit includes wire 260 leading through the solenoid coil 196, the other side of which is connected by the wire 262 to the other power line 201. Hence if either of the coils 225 and 237 is energized, the circuit will be closed both for the Y motor and the solenoid lock.

The X motor circuitry is the counterpart of the Y motor circuitry. It includes a manual X motor switch 265 connected from the power line 205. Closure of the switch 265 connects a wire 266 to a coil 267 also known as R3. The other side of this coil is connected by a wire 268 to the wire 226 so that it is controlled by the circuitry of the double-throw switch 210 as well as the pre-set count relay switch 207a, just as the Y motor circuitry is controlled by them. The coil 267 controls relay switches 267a and 267b, 267c and 267d. The normally closed switch 267a connects a wire 270 from the power line 205 to a relay coil 271, also known as R4. This coil controls a switch 271a as well as the reversing network switches 271b, 271c, 271d and 271e, that regulate the direction of current through the field winding of the X axis motor 60. The other end of the coil 271 is connected by a wire 272 to an X motor center switch 273 that is normally closed except when the X motor is in its central starting position. The switch 273 is connected by a wire 274 to the other power line 201.

The relay switch 267b connects the power line 205, by a wire 275 to the speed control 278 corresponding to the Y-motor speed control 246. Its output wire 279 leads into the reversing network which operates in the same way as the Y motor reversing network by selective operation of the relay switches 271b–271e, under control of the core 271, to deliver current to the field winding 280 of the X motor 60 in the forward or reverse direction. The other side of the motor 60 is connected by wire 282 to the other power line 201.

The speed control network for the X motor includes the normally-open relay switch 267c that connects to the adjustable resistance 284 (see adjusting knob 284, FIG. 1) and the normally-closed switch 267d that connects to the internally pre-settable resistor adjuster 285.

The solenoid lock for the X motor 60 is connected by a wire 287 that is energized through either of the two relay switches 267b or 271a; either, when closed, puts the solenoid coil 186 into circuit by the wire 287 and a wire 288 to the power line 201.

A calibrating connector circuit is provided to enable the motor speed controls to be checked and calibrated to the dials of knobs 249 and 284. This includes a wire 290 connected to the wire 205 (here a little below the Y-motor switch 223). The wire 290 leads to a counter 291 and thence to a manual selector switch 292 that can be open, or connected to either a wire 293 leading to the X-axis wire 214 or to a wire 294 leading to the Y-axis wire 217. As will appear, the counter 291 is then made subject to either of the pulsing switches 214 and 218.

OPERATION

The machine is designed for evaluating the cleaning, polishing, abrasion, and scratching ability of dentifrices or dentifrice abrasives, as well as other tooth-affecting agents, such as prophylactic pastes or mouthwashes containing polishing agents. This brush-testing operation can be performed on either human teeth, animal teeth, or artificial or synthetic substances that have characteristics equivalent to those of human enamel, dentin or cementum. Each tooth, or portion thereof, is mounted in a suitable material to form the specimen S, with the labial surface of the tooth exposed. For use in evaluating abrasion, exposed radioactive dentin from the root surface is used. Several such specimens are provided as the machine can handle six at a time, or any number less than that. Clearly, it could be designed to handle more or fewer if desired.

With the brush supports 138 detached from the machine, the specimen vises 49 are exposed beneath the X and Y axis platforms 97 and 106 (see the third station view in FIG. 1), so that with the screws 58 loose, the specimens S can be inserted over the ledges 55 and clamped firmly into place between the ledges 55 and the clamp plates 56 by turning the screws 58 down.

If it is more convenient, the vises 49 can be removed from the holders 35. When the screws 51 are loosened, and the screws 50 are removed from engagement with the specimen vises 49, the vises can be dropped downwardly to be freed from their carriers 35, the action withdrawing the notches at the top of the vises from the screws. After the specimens are then mounted in the vises, the vises are readily replaced on the carriers 35 by the reverse operation.

When the suitable test brushes have been selected, they are installed on the brush carriers 138. These carriers are removed from the machine by loosening the knurled screws 150 and dropping the carriers 138 downwardly until the screws 150 are free of the notches 139 and the notches 141 can pass over the heads of the clamp screws 151.

To mount a brush, it is laid over its carrier 138 with its bristles passing through the hole 140. A brush clamp 143 is inserted over the end of the brush carrier 138 so that its overhanging edges, as shown in FIG. 10, engage behind the edges of the brush holder 138. Then tightening the screw 147 pushes the somewhat flexible clamping blade 145 against the back of the brush in order to hold the brush securely in place, and at the same time to hold the brush clamp securely on the support. When assembled, each brush holder 138 with its brush is then reinstalled onto the Y axis platform 106 by having the notches 141 inserted over the heads 151 and the brush holder moved upwardly to displace the notches 141 from the heads 151 so that the lower end of the brush is clamped, and at the same time the notch 139 is moved under the screw 150 which is tightened down to hold the brush securely in place.

When the specimens and brushes are thus set up, the specimens are urged against the bristles of the brushes by the action of the weights 45. The beams 146 should be maintained approximately horizontal so that the total forces of the weights are applied to the specimens. Horizontality is obtained by adjusting the screws 47 with the specimens and brushes in place. When the beams 43 are horizontal, the lock nuts 48 are tightened. A very close adjustment of the force between each specimen and its brush can be obtained in this manner, it being remembered that the specimen holder 35 is mounted for very free horizontal movement because of the ball bushings 39.

Each of the cups 160 is supplied with an adequate amount of a suspension or solution containing the cleaning, abrading, polishing or other material to be tested. The quantity must be sufficient to immerse the specimen and the brush that extends down into each cup. The agitator 155 of flexible plastic will be moved with the motion of the brush in order to maintain the material being tested stirred up.

With all of the specimens mounted and the cups duly charged with the liquid, the degrees of motion in the X and Y axes are determined. As is illustrated, this is performed by adjusting the distances from the center of the two wheels 62 and 109 at which their connecting links 64 and 110 are connected. Preferably this can be accomplished by supplying screw holes at different positions out from the axis of the respective wheel, or if infinite adjustment is required, a slot such as the slot 112 can be provided. The several holes are preferred because there is no chance of slippage with such connections. In either case, the attaching screws for the links are loosened, then properly located on their respective wheels, and re-tightened. Such connections being well-known, they need not be described in detail.

It may be that movement in only one of the two axes is desired, or that different degrees of movement in one axis from that in the other are needed. If greater movement in one axis is desired over that in the other, it is simply a matter of the relative positions of the screws in the two wheels 62 and 109. If it is desired to operate in only one of the axes, that is preferably performed electrically in a manner to be described.

After the machine is set up in order to provide the proper amounts of movement in each direction, the speeds of operation of the two X and Y axis motors are individually selected by adjusting the two knobs 249 and 284 on the control panel 24. The dials are calibrated for convenience.

The control is designed to operate until a predetermined number of cycles have been performed. The control can be either as a count of the number of X axis cycles, or Y axis cycles. Normally the faster-moving motor will be used as the control and, in the description to follow, it shall be assumed that the X axis motor is running faster and that the counters will count its cycles. This simply requires that the switch 213 be set in the X direction, which is the one illustrated in FIGS. 1 and 11.

The number of cycles to be run is determined by a pre-set counter 300 on the panel 24. This counter includes the coil 207. As shown, it has five digits, which for illustration have been set so that the machine will run 34,678 cycles. There is a push button 301 for each of the digit dials. The user individually pre-sets these buttons 301 to bring up the desired digit for their particular dials, which will then be the number of cycles that will be operated before the machine stops. The clearing button 302 can be used to return all of the dials to zero. This is a commercial counter, and there are a number available on the market. The one here chosen is a Durant.

The switch 210 is shown on the panel 24. Normally it is in the upper position in the wiring diagram so that the pre-set counter operates. However, it can be swung to the lower position, closing together the contacts 228 and 229 and bypassing the counting mechanism.

There is a cycle counter 306 on the panel 24. This counts the number of cycles that have been performed by the machine after a given zeroizing has been accomplished. This counter is zeroized by a push button 307. It also is a commercially obtainable counter, such as a Durant.

To initiate the electrical mechanism, the master switch 204 on the panel 24 is closed manually. The switch 210 is in its normal upper position in the wiring diagram and, as noted, the switch 213 is in its X master position. The switch 292 is in its neutral position. At this time the Y motor switch 223 and the X motor switch 265 are both open. The relay coil 225 is thus de-energized as is the relay coil 267. The circuits to the Y motor 107 and the X motor 60 are both open. The circuits to the coil 237 and the coil 271 are both open because the Y and X motor center switches 242 and 273 have been opened by the previous operation. The locks are engaged in locking position because the solenoid lock coils 196 and 186 are de-energized. The switches 215 and 218, which are the X and Y pulse switches, are open because the X and Y motors are in their starting positions.

It will be assumed that an operation is desired in which both the X and the Y motors operate so that the motion of the brushes over the specimen is a compound motion in the vertical plane. It will be understood, however, that either of the two motors can be operated separately, producing linear motion in either the X or the Y direction.

Assuming that the manual switches 223 and 265 are closed, the following sequence occurs: closure of the switch 223 provides a circuit for the relay coil 225 through the normally-closed relay switch 207a since at the starting of the machine, the coil 207 is not in a closed circuit because the switch 215 is open. And setting of the pre-set counter 300 away from zero automatically breaks the circuit to the coil 207 internally of the control and holds that circuit open until the pre-set counter 300 has returned to its zero position after the pre-set number of cycles have been performed.

Energization of the relay coil 225 shifts the relay switches 225a through 225d with the following results: first the circuit through the switch 225a to the relay coil 237 is opened at the switch 225a. This circuit was already opened at the Y motor center switch 242. Second, the switches 225b and 225c are closed and the switch 225d is opened. This provides a circuit into the speed control 246 which has been pre-set by adjustment of the knob 249. The circuit is closed through the relay switch 225b, the speed control, the resistance 249, and by the wire 251 to the reversing network. The circuit to the field winding 253 continues from the wire 251 through the normally-closed relay switch 237c, field winding 253, normally-closed relay switch 237d and the motor 107, which is caused to operate in a forward direction. At the same time the reverse speed-adjusting resistor control 250 (which is internal of the control) is taken out of circuit by opening of the relay switch 225d, and the switches 237b and 237e open the reverse field winding circuitry.

At the time the foregoing circuit is energized, the solenoid lock coil 196 is also energized, since it comes from the wire 245 by way of the wire 260 that is connected to the power line 205 when the relay switch 225b is closed. This disengages the solenoid lock pin 193 from the hole 194 in the link 116 to permit the motor to operate the mechanism. The Y motor 107 is thus put into operation in a forward direction.

In like manner, the closure of the X switch 265 energizes the relay coil 267 by the circuit which also connects by the wire 268 to the pre-set relay switch 207a which, for reasons above explained, is now closed. Energization of the coil 267 opens the relay switch 267a to take the relay coil 271 out of circuit. It was not at that time energized because the X motor centering switch was open. Energization of the relay 267 also closes the switch 267b which provides a circuit by the wire 275 to X-axis speed control 278, and in addition closes the relay switch 267c and opens the relay switch 267d. The closure of the switch 267c at this time sets the speed control circuit for the running or forward direction of the X motor 60, and opening of the switch 267d opens the speed control circuit for reverse operation of the motor. The circuit to the motor is completed from the wire 279 through the now-closed relay switch 271c upwardly through the field winding 280, through the now-closed relay switch 271d and the motor 60. When the relay switch 267b is closed, solenoid lock coil 186 is also energized from the wires 275 and 287 to draw the lock pin 183 out of the hole 184 and to permit the H-bar 69 to rock.

Thus, the two motors 60 and 107 are put into operation at predetermined speeds. Each time the X motor completes a revolution, it momentarily closes the switch 215 which pulses the pre-set count device 300 one step down toward zero and also operates the cycle count 306 to advance its numbering one unit.

Each time the Y motor makes a revolution, it also closes the Y master switch 218. This has no effect because the master switch 213 was set for control by the X motor rather than the Y motor. However, if that switch had been in the other position, the opposite condition would have resulted with control by the total number of revolutions of the Y motor.

The foregoing operation will continue until pre-set count in the counter 300 has returned to zero plus one, at which time the relay coil 207 is energized (through its internal switching) by the final pulse that closes the switch 215. This opens the relay switch 207a that controls both the X motor and the Y motor circuits. The coils 225 and 267 are then de-energized and the motors stop.

When the pre-set counter, by returning to its zero position, opens the relay switch 207a, de-energizing the relay coils 225 and 267, both motors are stopped by the dropping-out of the relay switches 225b and 267b. At the same time, the switches 225a and 267a are closed. Closure of the switch 225a at this time normally energizes the coil 237 because the Y motor centering switch 242 is then closed unless, by sheer happenstance, the Y motor has stopped in its exact center position. Energization of the coil 237 closes the switch 237a which can re-start the motor 107 but in the opposite direction and at a different rate of speed. Because the relay 225 is now de-energized, the relay switch 225c is open and the switch 225b is closed. This means that the speed-regulating circuit 250 is now in control of the motor. Also, the energization of the relay 237 reverses the relay switches 237b–237e so that the field winding is now energized by the wire 205, the switch 237a, the wire 260 and 245, the speed control 246, the wire 251 to switch 237b downward, the field winding 253 and the relay switch 237e to the motor 107. This causes the motor 107 to operate in a reverse direction at a predetermined reversing speed.

The motor 107 operates in a reverse direction only until it has moved the linkage to its center position, at which point the switch 242 is automatically opened. This de-energizes the coil 237, opening the relay switch 237a and stopping the motor 107. It also de-energizes the solenoid coil 196 and permits the solenoid lock pin to again engage into the hole 194 on the link 166 which is now in its center position.

In like fashion, the X motor 60 is operated in reverse until it automatically opens the switch 273, thereby releasing the relay coil 271 and its switches, and releasing the solenoid coil 186 so that the pin 183 is operated by the spring 182 into the hole 184. The motors will remain inoperative.

At this time the numbers on the pre-set counter 300 should equal the numbers originally pre-set on the cycle counter 306, assuming that the latter started at zero.

The mechanism can be re-started by re-setting the pre-set count to a new number, as this will cause a re-closure of the switch 207a accompanies by re-energization of the relay coils 225 and 267 to start a new operation.

Means are provided in order to calibrate the speeds of the motors. This can be understood by considering the X motor. The switch 292 is moved to the X side, closing with the wire 293. The switch 210 is moved to its lower position which, with the X motor switch 265 closed, energizes the coil 267, bypassing the switch 207a. Following the sequence previously described, this causes the X motor 60 to run at a speed set by the dial 284. Each time it runs, it pulses the switch 215 and this can operate a counter 291. The intervals, or number of counts per minute, can be checked with a stop watch and the knob 284 set to a corresponding position. In like fashion, the other dial can be set. As noted, the reverse direction speeds are internally adjusted, it not being necessary to have external indicators for that purpose.

The mechanical operation that is caused by the foregoing is as follows: The rotation of the X motor 60 rotates the wheel 62 at a predetermined rate of speed. This moves the link 64 which is attached to the H member 69. That member is rocked about the pivots 72 in the vertical partition 23, which lifts the cranks 80 that are connected to the end members 85 and 86 and therefore to the shaft 84 and the panel 95. The whole vertical platform 97 is reciprocated up and down on the two vertical rods 87 and 88.

The shafts 83 and 84 of the X axis platform also support, by the bearing blocks 100–105, the Y axis platform 106, upon which the several brushes are mounted. If the motor 107 is not operating, and its lock pin 193 is in the hole 194 of the link 116 (FIG. 7), there can be no horizontal movement by the Y axis motor 107, because the arm 123 is held immobile. However, the X axis movement can continue vertically by virtue of the sliding of the vertical shaft 125 in the sintered bearing 127. The foregoing will mean that the brushes are moved vertically up and down across the specimens S.

If, on the other hand, the Y axis motor 107 is also made operative and its locking pin 192 is withdrawn, that motor will rock the link 116 about the axis of the shaft 120, oscillating that shaft and the over arm 123 which, by engagement with the sintered bearing 127, can displace the pin 125 and hence the block 104 and Y axis platform 106 back and forth horizontally. The depth of the slot in the end of the arm 123 permits arcuate movement of the arm 123 although the Y axis platform must move in a straight line.

With the Y axis motor 107 operating alone, the Y axis platform simply reciprocates back and forth horizontally, on the X-axis platform 97, the latter remaining stationary and locked. With both motors running, the Y-axis platform 106 moves in a compound movement which can be either circular or oval, and if oval, it may have its major axis either vertical or horizontal. If the motors operate at different speeds, compound motions of other shapes may be produced.

In a typical arrangement of this machine, a cycle rate control can be from zero to 100 cycles per minute for each axis. While it has been noted that the brush pressure can be made uniform on all of the specimens, this is not necessary. In some tests it may be desired to determine the effect of different brushes and this can be performed by individually adjusting the weights on the several specimens. A typical stroke adjustment for the X axis is zero to 2.54 centimeters, and on the Y axis is zero to 1.27 centimeters.

It is desirable that the brush carriers be individually mountable for each station. Also the use of an individual brush clamp for each station can ensure parallelism between the brushes and the specimens.

This machine thus overcomes the disadvantages of the former cross brushing machine. The compound, non-rectilinear movement between brushes and specimens overcomes a serious drawback of the cross-brushing machine, in eliminating the linear grooves ground into the surfaces of the specimens by the repeated tracking of the brush back and forth over the same parts of these surfaces. When specimens subjected to cross-brush tracking are set into recording apparatus for indicating and recording the results produced by the cross-brushing machine on the specimens, the rectilinear grooves produce different responses to the test recorder apparatus with different orientations of the specimens in the recorder thus resulting in large deviations in results. The results of recording from specimens tracked circularly in the present machine are indifferent to the orientation of the specimens in the recorder.

Yet for purposes of directly comparing specimens against test results from the cross-brushing machine, the present machine can be easily set to produce cross-brushing, by keeping one motor inoperative.

The present machine maintains uniform pressure between the specimens and the brushes, by virtue of the arrangement of the gravity-operated scale-beam type force means. The weights 45 are set to obtain desired forces, and the screws 48 are adjusted after the brushes and specimens are set into their places in order to obtain maximum horizontality of the beams. The pressures thereby set will remain constant throughout the run of test cycles, the arrangement being free of fatigue problems and Hooke's law problems that affect the cross-brush machine, and unaffected by repetitive vibrations caused by the cycling operation. Obviously, this results in an increase in accuracy. The movements of the specimen holders being horizontal are free from the need for and problems of counterbalancing. This combination of horizontal movement and gravity-impressed forces also permits very accurate setting of light pressures that can be maintained throughout certain studies, for example, when polishing studies are studied, or for other tests which require longer periods of time, say for abrasion of enamel.

The agitators 155, that cycle with the brushes, and that dip to the bottoms of the cups 160, maintain the slurry suspensions in a homogeneous condition so that settling does not occur. This is aided by the fact that the motion of the agitators is toward and from the bottom, where settling would deposit solid particles from the slurry. The slurry containers having sloping sides which aid in having full abrasive pickup. Individual slurry buckets give greater flexibility to the machine and they are designed to insure that the specimen and the brushes are always wet with the slurry.

It is preferred that the machine be designed of aluminum, stainless-steel and brass for minimal deterioration; preferably the housing enclosure is aluminum, although it may be plastic. As noted, the slurry cups are preferably clear plastic. It will also be observed that the parts are accessible for ready repair and replacement, although the use of anti-friction bearings for both rotary and reciprocal parts insures long life without the necessity of repair.

Various changes and modifications may be made within this invention as will be readily apparent to those skilled in the art. Such changes and modifications are within the scope and teaching of this invention as defined by the claims appended hereto.

What is claimed is:

1. In a machine for applying rubbing tests to specimens, such as tests for the effects of polishing, cleaning, scratching and abrasion agents on human teeth, and the like: a base, a specimen holder means, a support means for supporting a rubbing device, the specimen holder means and the support means being mounted on the base in proximity so that a specimen on the holder means can be rubbed by the rubbing device and one of said means being laterally movable on the base relatively to the other, and driving mechanism for transversely moving the laterally movable one of the means relative to the other to produce a path of movement of the rubbing device across a specimen in the holder and return, the driving mechanism including means to cause the movement of the said laterally movable one of the means across the specimen to be in one path and its return movement to be in a different path, to reduce grooving of the specimen by repeated motion forth and back along the same path.

2. In the machine of claim 1: the driving mechanism having individual means for producing movements in two directions at right angles to each other, the movement producing means being individually adjustable to alter the displacements in each direction.

3. In the machine of claim 1: the driving mechanism, including mechanism to produce movement in two directions.

4. In the machine of claim 3: said laterally movable means including a first platform, means mounting the first platform on the base for movements thereon; a second platform, and means mounting the second platform on the first platform for movements relatively to the first platform, whereby the second platform may have compound movements relatively to the base.

5. In the machine of claim 4: the mounting means for at least one platform including linear track means, platform support means guidedly movable on the track means, the said one platform comprising a rigid framework.

6. In the machine of claim 4: each platform comprising a rigid framework, linear track means, and platform support means guidedly movable on the track means; the first platform track means being mounted on the base and the second platform track means being mounted on the first platform.

7. In the machine of claim 6: at least one brush holder means mounted on the second platform to constitute the support means for the rubbing device.

8. In the machine of claim 7: the brush holder means depending from the second platform, the specimen holder means being disposed adjacent the depending brush holder also below that second platform; and a liquid-holding cup to encompass the specimen holder and brush holder.

9. In the machine of claim 6: the driving mechanism comprising motor-driven means on the base for moving the platforms.

10. In the machine of claim 1: the base having a rigid panel; there being a plurality of specimen holder means mounted on that panel, and each comprising a pair of rods reciprocably mounted through the panel for linear movements, a holder bracket mounted on the rods for reciprocation toward and from one side of the panel; scale beam means on the opposite side of the panel engageable with one of the rods, including a beam and a weight adjustable along the beam, the scale beam means urging the rod and the holder bracket away from the panel with a yieldable force; each specimen holder means further comprising a specimen vise on the holder bracket, operable to clamp a specimen onto the bracket with exposure in the direction away from the bracket; said laterally movable means comprising a pair of vertical platform track rods at opposite sides of the machine, attached to one face of the panel, a first platform having platform supports reciprocable vertically along the track rods, and the first platform also including a pair of horizontal track rods connected between the platform supports; said laterally movable means further comprising a second platform including supports reciprocable horizontally along the horizontal track rods, and a second platform panel secured to and movable with those supports; the support means comprising a plurality of brush holders corresponding in number to the specimen holders and mounted on the second platform panel to extend opposite the specimen holders; said driving mechanism comprising a vertical motor on the base, drive means connecting the vertical motor to the first platform to reciprocate it vertically; a horizontal motor on the base, drive means connecting the horizontal motor to the second platform for moving it horizontally, and means for controlling the motors.

11. In the machine of claim 10: the drive means for at least one of the motors including means to adjust the amplitude of movement of the associated platform produced for each revolution of the motor.

12. In the machine of claim 10: means to adjust the speed of each platform drive means independently of the other.

13. In the machine of claim 10: lock means for each drive means to hold the associated platform in predetermined position; and means to release each lock means to permit the movement of the associated platform.

14. In the machine of claim 13: the release means being electrically operated and actuated upon energization of the associated motor.

15. In the machine of claim 1: the driving mechanism comprising an electric motor to produce the relative movements; a pre-settable counter to count cycles of the said movements, and to stop the motor after the pre-set number of cycles have been run; counter circuit means including a counter switch closed when the counter is pre-set and reopened when it has counted the run, the circuit means including a manual switch, and a relay coil, the coil being thus energized when the two said counter and manual switches are closed; forward circuitry and reversing circuitry for the motor; relay switch means operated by the relay coil to close in the forward circuitry when the relay coil is energized and to close in the reversing circuitry when the relay coil is deenergized, the reversing circuitry including a second relay coil and a motor center switch closed except when the machine is centered by the motor, and including relay switches in the motor circuit to reverse its direction of rotation, whereby when the forward movement attains its predetermined count the motor will stop and be reversed until the machine is centered, and then stop.

16. In the machine of claim 15: speed regulating means for the motor including two separate speed setting means, one for forward and one for reverse operations, means interposing the forward speed means in the forward circuitry for the motor, and means interposing the reverse speed means in the reversing circuitry.

17. In the machine of claim 15: the driving mechanism further comprising a second electric motor and control means therefor; said laterally movable means having mounting means on the base for movements in two directions; and means connecting each of said electric motors to the mounting means.

18. In the machine of claim 17: means selectively to connect the counter circuit means for operation by either one of the motors, so that it can count movements in either of the two directions.

19. In the machine of claim 18: a calibrating circuit connectable to operate each motor and counting means to check the rate of speed of the motor.

20. In the machine of claim 1: a liquid holding cup disposed adjacent the support for the rubbing device, the laterally movable one of said means having a flexible finger depending into the cup to agitate the liquid therein.

21. In the machine of claim 1: means for holding the laterally movable means and the said other means on the base in proximity and providing horizontal movement of the said other toward the laterally movable means with means urging the horizontally movable means toward the laterally movable means throughout the rubbing movement.

22. In a machine for applying rubbing tests to specimens, such as tests for the effects of polishing, cleaning, scratching, and abrasion agents on human teeth, and the like: a base, a specimen holder means, a support means for supporting a rubbing device, the specimen holder means and the support means being mounted on the base, in proximity, and one of said means being laterally movable relatively to the other so that a specimen on the holder means can be rubbed by the rubbing device, and driving mechanism for moving the laterally movable one of the means transversely relative to the other means to produce a path of movement of the rubbing device across a specimen in the holder and return, means for maintaining the support means and the specimen holder means in proximity, including a mounting for the said other of the two means that supports it for horizontal movement on the base, forward and backward relatively to the laterally movable means, and yieldable force means acting upon the horizontally movable means urging it toward the laterally movable means.

23. In the machine of claim 22: the base having a vertical member upstanding therefrom; a frictionless bearing supporting a shaft for horizontal axial movement on the vertical member; said yieldable force means comprising a scale beam mounted on the vertical member for rocking movements in a vertical plane, means for applying the beam forces axially to the shaft, and means for applying the force of the shaft to the horizontally movable means to urge it toward the laterally movable means.

24. In the machine of claim 23, the horizontally movable means being mounted on and at least partially supported by the shaft.

25. In a machine for applying rubbing tests to specimens, such as tests for the effects of polishing, cleaning, and abrasion agents on human teeth, and the like: a base, a specimen holder means, a support means for supporting a rubbing device, the specimen holder means and the support means being mounted on the base, in proximity and one of them being laterally movable relatively to the other so that a specimen on the holder means can be rubbed by the rubbing device, and driving mechanism for transversely moving the laterally movable one of the means relative to the other means to produce a path of movement of the rubbing device across a specimen in the holder and return, the driving mechanism for moving the laterally movable one of the two means providing vertical movement thereof, and liquid-agitating means depending from the laterally movable means.

26. In the machine of claim 25: the agitating means comprising a flexible strip attached to and extending from the lower end of the laterally movable 27. In a machine for testing abrasion, polishing and the like of specimens: a specimen support platform movable in two directions; two motors, each with a drive means connected to the platform to produce movement of the platform in one of said directions; and control mechanism for operating the motors; the control including: a pre-set counter pre-settable to register a predeterminable number of motor cycles; means including a manually operable means and the pre-set counter to operate each motor, and cause it to operate for a predetermined number of cycles of the pre-set counter; means to reverse the motors when the predetermined number of cycles have been performed; and means to stop the motors when the reverse operation has centered their drive means.

28. In a machine for testing abrasion, polishing and the like of specimens: a specimen support platform movable in two directions; two motors, each with a drive means connected to the platfform to produce movement of the platform in one of said directions; and control mechanism for operating the motors, the control including: a pre-set counter pre-settable to register a predeterminable number of motor cycles; means including a manually operable means and the pre-set counter to operate each motor, and cause it to operate for a predetermined number of cycles of the pre-set counter, and means to adjust the speed of each motor separately.

29. The machine of claim 28: with means to pre-set the speed of each motor separately, including means to control the forward speed independently of the reverse speed.

* * * * *